(12) United States Patent
Sharma et al.

(10) Patent No.: US 10,367,479 B2
(45) Date of Patent: Jul. 30, 2019

(54) METHOD AND APPARATUS TO REDUCE NOISE IN CT DATA ACQUISITION SYSTEMS

(71) Applicant: Texas Instruments Incorporated, Dallas, TX (US)

(72) Inventors: Rahul Sharma, Bangalore (IN); Vajeed Nimran, Bangalore (IN); Jagannathan Venkataraman, Bangalore (IN); Sandeep Kesrimal Oswal, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/980,791

(22) Filed: May 16, 2018

(65) Prior Publication Data

US 2018/0269856 A1     Sep. 20, 2018

Related U.S. Application Data

(63) Continuation of application No. 14/640,175, filed on Mar. 6, 2015, now abandoned.

(30) Foreign Application Priority Data

Mar. 6, 2014   (IN) ............................ 1146/CHE/2014

(51) Int. Cl.
| | | |
|---|---|---|
| *H03M 3/02* | (2006.01) | |
| *H03M 1/12* | (2006.01) | |
| *H03M 1/34* | (2006.01) | |
| *G11C 27/02* | (2006.01) | |
| *G06F 3/044* | (2006.01) | |
| *G06G 7/184* | (2006.01) | |
| *H03M 1/08* | (2006.01) | |
| *H03H 19/00* | (2006.01) | |
| *H03H 11/12* | (2006.01) | |
| *G01T 1/17* | (2006.01) | |
| *H02J 7/34* | (2006.01) | |
| *A61B 6/03* | (2006.01) | |
| *A61B 6/00* | (2006.01) | |

(52) U.S. Cl.
CPC ............. *H03H 19/004* (2013.01); *G01T 1/17* (2013.01); *H03H 11/1291* (2013.01); *A61B 6/032* (2013.01); *A61B 6/4208* (2013.01); *H02J 7/345* (2013.01)

(58) Field of Classification Search
CPC .... H03H 19/004; H03H 11/1291; G01T 1/17; A61B 6/032; A61B 6/4208
USPC ..... 327/108–112, 379, 389, 391; 326/22–27, 326/81–87
See application file for complete search history.

(56) References Cited

U.S. PATENT DOCUMENTS

5,030,954 A   7/1991  Ribner
5,117,227 A   5/1992  Goeke
(Continued)

*Primary Examiner* — Brandon S Cole
(74) *Attorney, Agent, or Firm* — John R. Pessetto; Charles A. Brill; Frank D. Cimino (57) ABSTRACT

The disclosure provides a circuit that includes an integrator that generates an integrated signal in response to a current signal. A comparator is coupled to the integrator and receives the integrated signal and a primary reference voltage signal. The comparator generates a feedback signal. A switched capacitor network is coupled across the integrator. The feedback signal activates the switched capacitor network.

15 Claims, 7 Drawing Sheets

(56) References Cited

U.S. PATENT DOCUMENTS

| | | | | |
|---|---|---|---|---|
| 6,351,506 | B1* | 2/2002 | Lewicki | H03H 19/004 |
| | | | | 327/337 |
| 6,819,281 | B2 | 11/2004 | Fujita et al. | |
| 8,575,988 | B2 | 11/2013 | Erdogan et al. | |
| 8,659,343 | B2 | 2/2014 | Erdogan et al. | |
| 9,654,135 | B2* | 5/2017 | Miki | H03M 1/468 |
| 2005/0184895 | A1 | 8/2005 | Petersen et al. | |
| 2006/0244650 | A1* | 11/2006 | Oprescu | H03M 3/322 |
| | | | | 341/155 |
| 2008/0068241 | A1* | 3/2008 | Hong | H03M 3/362 |
| | | | | 341/143 |
| 2008/0240316 | A1* | 10/2008 | Yokoshima | H04B 1/0021 |
| | | | | 375/350 |
| 2009/0146735 | A1* | 6/2009 | Jeong | H03F 3/005 |
| | | | | 327/554 |
| 2009/0195423 | A1 | 8/2009 | Li | |
| 2011/0050289 | A1* | 3/2011 | Lee | H03K 19/00384 |
| | | | | 327/108 |
| 2012/0161846 | A1 | 6/2012 | Ningrat | |
| 2012/0218020 | A1 | 8/2012 | Erdogan et al. | |
| 2013/0278538 | A1 | 10/2013 | Brunet et al. | |
| 2013/0329853 | A1* | 12/2013 | Coln | G06G 7/186 |
| | | | | 378/19 |
| 2014/0167995 | A1* | 6/2014 | Tiew | H03M 3/30 |
| | | | | 341/143 |
| 2014/0192360 | A1 | 7/2014 | Atzler et al. | |
| 2016/0149586 | A1* | 5/2016 | Roh | H03M 3/39 |
| | | | | 341/143 |

* cited by examiner

METHOD AND APPARATUS TO REDUCE NOISE IN CT DATA ACQUISITION SYSTEMS

CROSS REFERENCE TO RELATED APPLICATIONS

This continuation application claims priority to U.S. patent application Ser. No. 14/640,175, filed Mar. 6, 2015, which application claims priority to India provisional patent application No. 1146/CHE/2014, filed Mar. 6, 2014, both of which are hereby incorporated by reference in their entirety.

TECHNICAL FIELD

The present disclosure is generally related to medical diagnostic devices, and more particularly to reducing noise in computed tomography (CT) data acquisition systems.

BACKGROUND

Computed tomography (CT) is a medical imaging technique that produces three-dimensional images of internal human body parts from a large series of two-dimensional X-ray images (called profiles) taken in a single-axis rotating structure called a gantry. When compared to a conventional X-ray radiograph, which is an image of many planes superimposed on each other, a CT image exhibits significantly improved contrast.

With the advent of diagnostic imaging systems like CT, where complex and intensive image processing is required, semiconductors play a very important role in developing systems with increased density, flexibility and high performance. The helical or spiral CT machines that use faster computer systems and optimized software can continuously process the cross-section images while the object passes through the gantry at a constant speed.

X-ray slice data is generated using an X-ray source that rotates around the object, with X-ray detectors positioned on the opposite side of the circle from the X-ray source. Many data scans are taken progressively as the patient/object is gradually passed through the gantry. A scintillator receives x-rays attenuated by the patient and generates light. A data acquisition system includes a plurality of detectors or channels.

A detector receives the light form the scintillator and generates a corresponding current signal which is further converted to a digital signal. Since, the x-rays emitted by the x-ray source undergo attenuation while passing through the patient, not all the detectors of the plurality of detectors receive a large signal. Most of the detectors receive a very small attenuated signal (less than 10-15% of the signal emitted by the x-ray source).

Traditional, data acquisition systems provide a fixed gain for all the detectors of the plurality of detectors. This causes noise to be high for all the channels, and even for those channels which receive the very small attenuated signal.

SUMMARY

According to an aspect of the disclosure, a circuit is disclosed. The circuit includes an integrator that generates an integrated signal in response to a current signal. A comparator is coupled to the integrator and receives the integrated signal and a primary reference voltage signal. The comparator generates a feedback signal. A switched capacitor network is coupled across the integrator. The feedback signal activates the switched capacitor network.

DETAILED DESCRIPTION OF THE EMBODIMENTS

Figure 1:
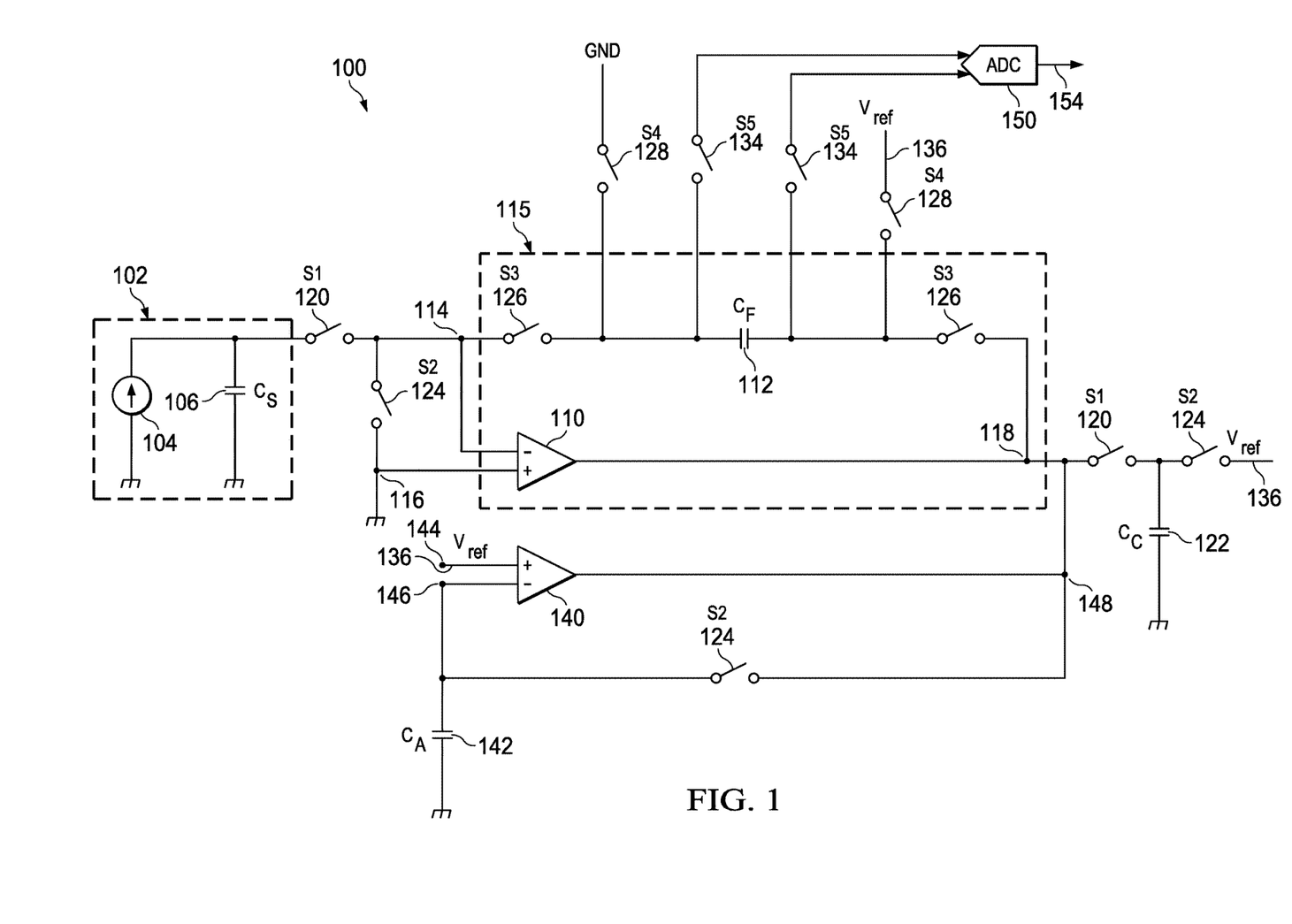
FIG. 1 illustrates a circuit.

FIG. 1 illustrates a circuit 100. The circuit 100 includes a photodiode 102, an integrator 115, a compensation capacitor Cc 122, a secondary transconductor 140 and an analog to digital converter (ADC) 150. The circuit 100 also includes a set of first switches illustrated as S1 120, a set of second switches illustrated as S2 124, a set of third switches illustrated as S3 126, a set of fourth switches illustrated as S4 128 and a set of fifth switches illustrated as S5 134.

The photodiode 102 includes a sensor 104 and an associated capacitance Cs 106. The integrator 115 is coupled to the photodiode 102 through the first switch S1 120. The integrator 115 includes a primary transconductor 110 with an inverting terminal 114 and a non-inverting terminal 116. The photodiode 102 is coupled to the inverting terminal 114 of primary transconductor 110. A non-inverting terminal 116 of the primary transconductor 110 is coupled to a ground terminal. A second switch S2 is coupled between the inverting terminal 114 and the non-inverting terminal 116 of the primary transconductor 110.

A feedback capacitor $C_F$ 112 is coupled between the inverting terminal 114 and a first output terminal 118 of the primary transconductor 110. The feedback capacitor $C_F$ 112 is coupled to the inverting terminal 114 through the third switch S3 126, and the feedback capacitor $C_F$ 112 is coupled to the first output terminal 118 through the third switch S3 126.

The feedback capacitor $C_F$ 112 is also coupled to a reference voltage signal Vref 136 and a ground terminal GND through fourth switches S4 128. The ADC 150 is coupled across the feedback capacitor $C_F$ 112 through the fifth switches S5 134. The compensation capacitor Cc 122 is coupled to the first output terminal 118 of the primary transconductor 110 through the first switch S1 120. The compensation capacitor Cc 122 is coupled to the reference voltage signal Vref 136 through the second switch S2 124.

The secondary transconductor 140 receives the reference voltage signal Vref 136 at a first input terminal 144. A second input terminal 146 of the secondary transconductor 140 is coupled to a first capacitor $C_A$ 142. The other end of first capacitor $C_A$ 142 is coupled to the ground terminal. The second input terminal 146 is coupled to an output terminal 148 of the secondary transconductor 140 through the second switch S2 124. The output terminal 148 of the secondary transconductor 140 is coupled to the first output terminal 118 of the primary transconductor 110.

The operation of the circuit 100 illustrated in FIG. 1 is explained now. The photodiode 102 receives light and generates a corresponding current signal. The sensor 104 receives the light and the associated capacitance Cs 106 stores a charge corresponding to the received light. The circuit 100 operates in a reset phase, an integration phase and a sample phase.

In the reset phase, the set of second switches S2 124 and the set of fourth switches S4 128 are closed. When the switch S2 124 is closed, the inverting terminal 114 and the non-inverting terminal 116 of the primary transconductor 110 are coupled to the ground terminal. An offset associated with the primary transconductor 110 will result in a current flowing from the first output terminal 118 of the primary transconductor 110.

A corresponding voltage develops at the second input terminal 146 of the secondary transconductor 140 and is stored in the first capacitor $C_A$ 142. Since, the fourth switch S4 128 is closed, the feedback capacitor $C_F$ 112 is charged to the reference voltage signal Vref 136. Also, the compensation capacitor Cc 122 is charged to the reference voltage signal Vref 136.

In the integration phase, the set of first switches S1 120 and the set of third switches S3 126 are closed, while other switches are in open state. The photodiode 102 generates the current signal based on the received light. The integrator 115 receives the current signal from the photodiode 102 at the inverting terminal 114 of the primary transconductor 110.

The integrator 115 generates an integrated signal at the first output terminal 118 of the primary transconductor 110. The secondary transconductor 140 compensates the offset associated with the primary transconductor 110. The integrator 115 integrates the current signal on the feedback capacitor $C_F$ 112. The feedback capacitor $C_F$ 112 discharges through the photodiode 102. At the end of integration phase, a voltage across the feedback capacitor $C_F$ 112 is a sampled voltage.

In the sample phase, the set of fifth switches S5 134 are closed, while other switches are in open state. The ADC 150 measures the sampled voltage across the feedback capacitor $C_F$ 112. The ADC 150 generates a digital signal 154 from the sample voltage.

A total noise of the circuit 100 is defined as:

$$N = N_{reset} + N_{int} + N_{adc} \quad (1)$$

where, $N_{reset}$ is a noise of the circuit 100 in the reset phase, $N_{int}$ is a noise of the circuit 100 in the integration phase, and $N_{adc}$ is a noise of the circuit 100 in the sample phase.

The noise in the reset phase, the integration phase and the sample phase are defined as:

$$N_{reset} = kT*C_F + 4*kT*BW*(1/g_{m\_in})*C_S^2 \quad (2)$$

$$N_{int} = 4*kT/C_{COMP}*\beta*C_S^2 \quad (3)$$

$$N_{adc} = C_F^2*V_N^2 \quad (4)$$

where, T is temperature, k is Boltzmann constant, $g_{m\_in}$ is transconductance of the primary transconductor 110 and BW is a bandwidth of the secondary transconductor 140 which is used for compensating the offset associated with the primary transconductor 110. $V_N$ is a noise of the ADC 150. Also, $$\beta = C_F/(C_F + C_S) \quad (5)$$

$$C_{COMP} = C_C + C_F*C_S/(C_F + C_S) \quad (6)$$

As illustrated in the above equations, the total noise of the circuit 100 is reduced if a value of the feedback capacitor $C_F$ 112 is reduced. In one example, an output of the integrator 115 swigs 4 volts. Hence for 200 pC range, a value of the feedback capacitor $C_F$ 112 is 25 pF and a value of the associated capacitance Cs 106 is 30 pF.

Figure 2:
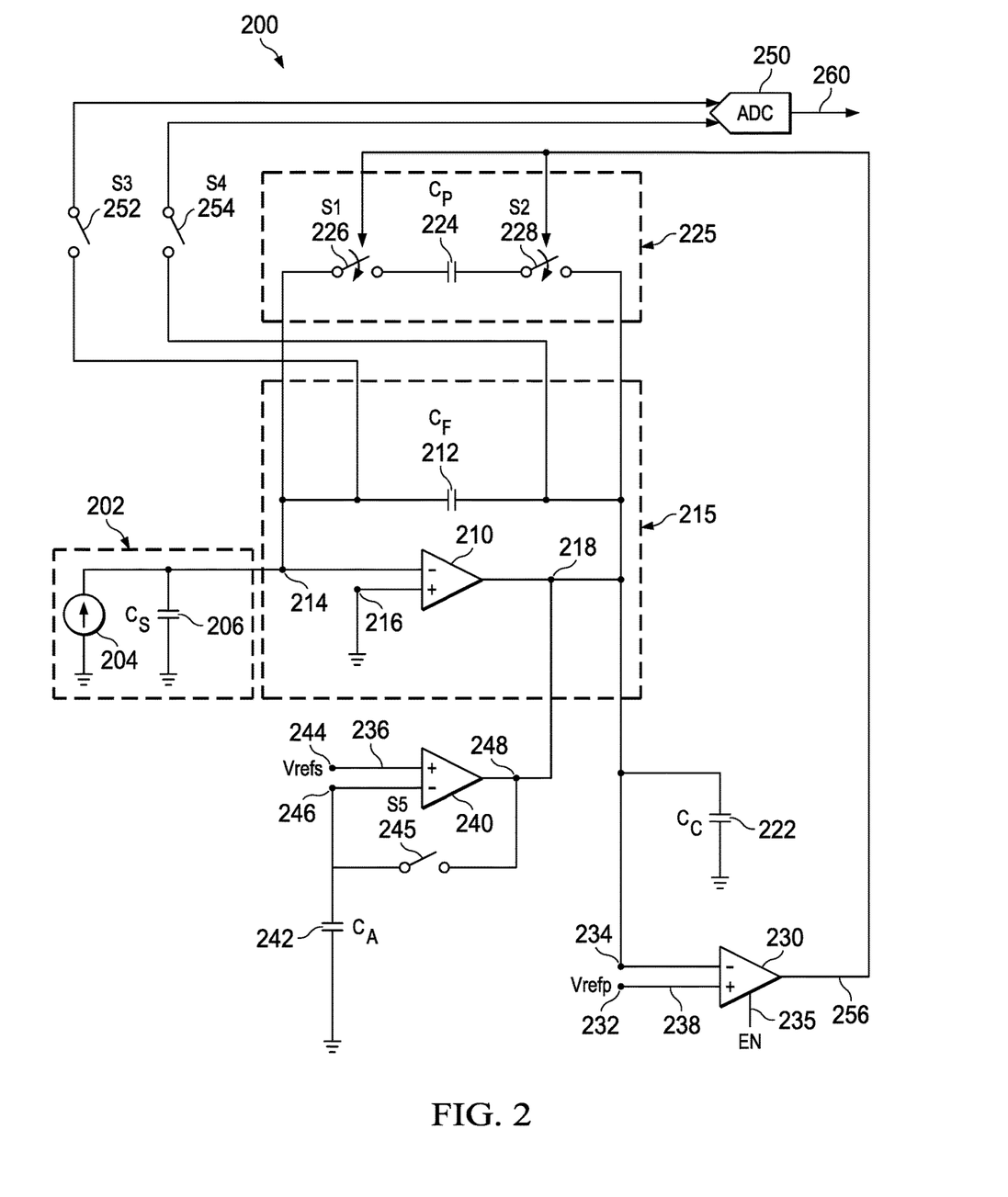
FIG. 2 illustrates a circuit, according to an embodiment.

FIG. 2 illustrates a circuit 200, according to an embodiment. The circuit 200 includes a photodiode 202, an integrator 215, a comparator 230, a secondary transconductor 240, a switched capacitor network 225 and an analog to digital converter (ADC) 250. The photodiode 202 includes a sensor 204 and an associated capacitance Cs 206. The integrator 215 is coupled to the photodiode 202.

The integrator 215 includes a primary transconductor 210 with an inverting terminal 214 and a non-inverting terminal 216. The photodiode 202 is coupled to the inverting terminal 214 of primary transconductor 210. A non-inverting terminal 216 of the primary transconductor 210 is coupled to a ground terminal.

A feedback capacitor $C_F$ 212 is coupled between the inverting terminal 214 and a first output terminal 218 of the primary transconductor 210. In one version, the feedback capacitor $C_F$ 212 is also coupled to a secondary reference voltage signal Vrefs 236 and a ground terminal through switches. The ADC 250 is coupled across the feedback capacitor $C_F$ 212 through a third switch S3 252 and a fourth switch S4 254.

The compensation capacitor Cc 222 is coupled to the first output terminal 218 of the primary transconductor 210. In one example, the compensation capacitor Cc 222 is coupled to the secondary reference voltage signal Vrefs 236 through a switch.

The secondary transconductor 240 receives the secondary reference voltage signal Vrefs 236 at a first input terminal 244. A second input terminal 246 of the secondary transconductor 240 is coupled to a first capacitor $C_A$ 242. The other end of first capacitor $C_A$ 242 is coupled to the ground terminal. The second input terminal 246 is coupled to an output terminal 248 of the secondary transconductor 240 through a fifth switch S5 245. The output terminal 248 of the secondary transconductor 240 is coupled to the first output terminal 218 of the primary transconductor 210.

A comparator 230 is coupled to the integrator 215. A first inverting terminal 234 of the comparator 230 is coupled to the first output terminal 218 of the primary transconductor 210. A first non-inverting terminal 232 of the comparator 230 receives a primary reference voltage signal Vrefp 238. The comparator 230 also receives an enable signal EN 235.

A switched capacitor network 225 is coupled across the integrator 215. The switched capacitor network 225 is coupled between the inverting terminal 214 and the first output terminal 218 of the primary transconductor 210. The switched capacitor network 225 includes a first input switch S1 226, a first output switch S2 228 and a primary capacitor Cp 224 coupled between the first input switch S1 226 and the first output switch S2 228.

The first input switch S1 226 is coupled to the inverting terminal 214 of the primary transconductor 210. The first output switch S2 228 is coupled to the first output terminal 218 of the primary transconductor 210. The circuit 200 may include one or more additional components known to those skilled in the relevant art and are not discussed here for simplicity of the description.

The operation of the circuit 200 illustrated in FIG. 2 is explained now. The photodiode 202 receives light and generates a corresponding current signal. The sensor 204 receives the light and the associated capacitance Cs 206 stores a charge corresponding to the received light. The circuit 200 operates in a reset phase, an integration phase and a sample phase.

In the beginning, all the switches (the first switch S1 226, the second switch S2 228, the third switch S3 252, the fourth switch S4 254 and the fifth switch S5 245) are in open state. In the reset phase, the fifth switch S5 245 is closed. The inverting terminal 214 of the primary transconductor 210 is coupled to the ground terminal. An offset associated with the primary transconductor 210 will result in a current flowing from the first output terminal 218 of the primary transconductor 210 to the first capacitor $C_A$ 242.

A corresponding voltage develops at the second input terminal 246 of the secondary transconductor 240 and is stored in the first capacitor $C_A$ 242. Thus, the offset associated with the primary transconductor 210 is stored at an input of the secondary transconductor 240.

The feedback capacitor $C_F$ 212 is charged to the secondary reference voltage signal Vrefs 236. Also, the compensation capacitor Cc 222 is charged to the secondary reference voltage signal Vrefs 236. The primary capacitor Cp 224 in the switched capacitor network 225 is charged to the primary reference voltage signal Vrefp 238.

In the integration phase, the photodiode 202 generates the current signal based on the received light. The integrator 215 receives the current signal from the photodiode 202 at the inverting terminal 214 of the primary transconductor 210. In one version, the integrator 215 receives the current signal from a device coupled to the integrator 215.

The integrator 215 generates an integrated signal at the first output terminal 218 of the primary transconductor 210. The secondary transconductor 240 compensates the offset associated with the primary transconductor 210. The integrator 215 integrates the current signal on the feedback capacitor $C_F$ 212. The feedback capacitor $C_F$ 212 discharges through the photodiode 202. In one version, the feedback capacitor $C_F$ 212 and the compensation capacitor Cc 222 both discharge through the photodiode 202. The compensation capacitor Cc 222 reduces the noise of the circuit 200.

The comparator 230 receives the integrated signal from the integrator 215. The comparator 230 is activated by the enable signal EN 235 for a defined time period. In one example, the defined time period (T) is computed as:

$$T = \frac{Vrefs - Vrefp}{2 \times Vrefs} \quad (7)$$

The comparator 230 compares the integrated signal and the primary reference voltage signal Vrefp 238. If the integrated signal is below the primary reference voltage signal Vrefp 238 during the defined time period, the comparator 230 generates a feedback signal 256. The feedback signal 256 activates the switched capacitor network 225. The feedback signal 256 activates the first input switch S1 226 and the first output switch S2 228. Thus, the primary capacitor Cp 224 is coupled in parallel to the feedback capacitor $C_F$ 212.

As the primary capacitor Cp 224 is charged to the primary reference voltage signal Vrefp 238 in the reset phase, addition of the primary capacitor Cp 224 in the circuit 200 does not introduce any glitch at the inverting terminal 214 and the non-inverting terminal 216 of the primary transconductor 210. This ensures that the current signal from the photodiode 202 is not affected by addition of the primary capacitor Cp 224.

If the integrated signal is above the primary reference voltage signal Vrefp 238 during the defined time period, the comparator 230 does not generate the feedback signal 256 and hence, the first input switch S1 226 and the first output switch S2 228 are not activated. In one version, when the terminal of the comparator 230 are interchanged, then, if the integrated signal is above the primary reference voltage signal Vrefp 238 during the defined time period, the comparator 230 generates the feedback signal 256, to activate the first input switch S1 226 and the first output switch S2 228. At the end of integration phase, a voltage across the feedback capacitor $C_F$ 212 is a sampled voltage.

In the sample phase, the third switch S3 252 and the fourth switch S4 254 are closed, while other switches are in open state. The ADC 250 measures the sampled voltage across the feedback capacitor $C_F$ 212. The ADC 250 generates a digital signal 260 from the sample voltage.

As discussed in connection with circuit 100, illustrated in FIG. 1, the total noise of the circuit is reduced if a value of the feedback capacitor $C_F$ is reduced. This is also illustrated in equations 1 to 6. The circuit 200 provides a low value of the feedback capacitor $C_F$ 212. In one example, the feedback capacitor $C_F$ 212 is 4 pF. Thus, in the integration phase, initially only the feedback capacitor $C_F$ 212 discharges through the photodiode 202.

The integrator 215 generates the integrated signal, and when the integrated signal is below the primary reference voltage signal Vrefp 238, the primary capacitor Cp 224 also starts discharging through the photodiode 202. Thus, the current signal is integrated at the feedback capacitor $C_F$ 212 and the primary capacitor Cp 224.

In one example, the secondary reference voltage signal Vrefs 236 is less than the primary reference voltage signal Vrefp 238. Since, in the reset phase, the feedback capacitor $C_F$ 212 is charged to the secondary reference voltage signal Vrefs 236, when the primary capacitor Cp 224 is coupled in parallel to the feedback capacitor $C_F$ 212, a potential across both these capacitors is equal to the secondary reference voltage signal Vrefs 236. Thus, a voltage glitch at the inverting terminal 214 of the primary transconductor 210 is very low.

When a level of the current signal is low, the comparator 230 does not generate the feedback signal 256, and thus, only the feedback capacitor $C_F$ 212 is part of the circuit 200 in integration phase. This drastically reduces a noise of a system using the circuit 200. The circuit 200, in one embodiment, is used in a data acquisition system to provide variable gain to each detector of the plurality of detectors based on the received current signal.

Figure 3:
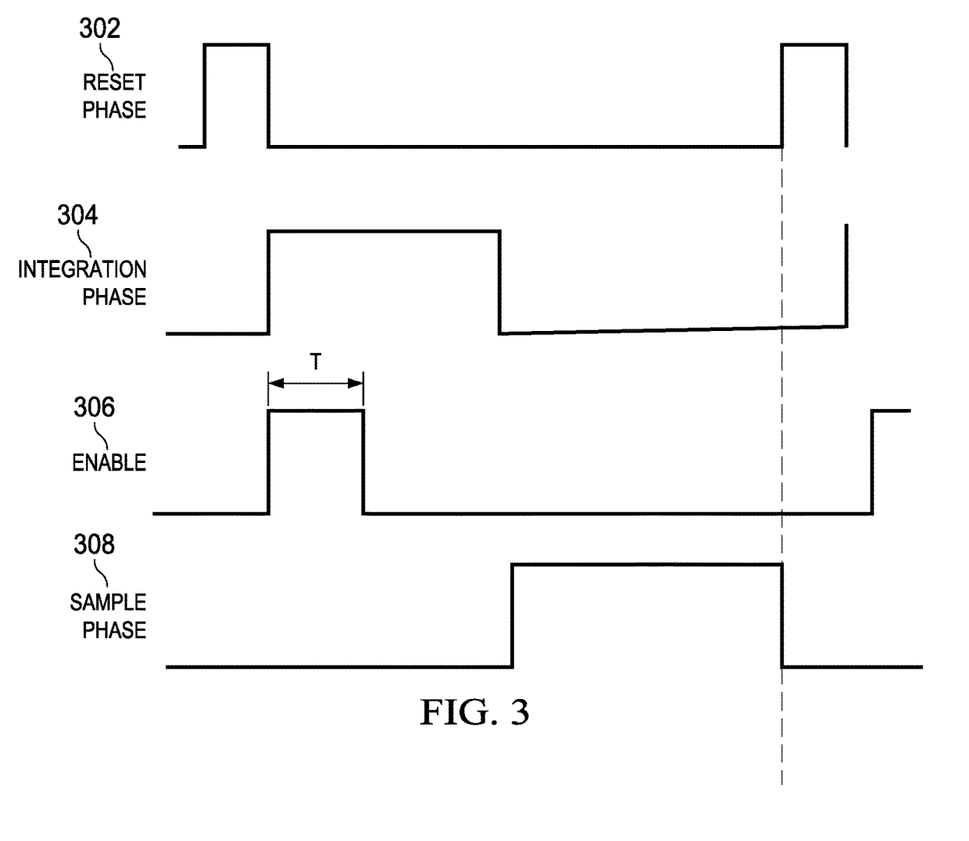
FIG. 3 is a timing diagram to illustrate the operation of the circuit illustrated in FIG. 2, according to an embodiment.

FIG. 3 is a timing diagram to illustrate the operation of the circuit 200, according to an embodiment. The timing diagram illustrates a reset phase 302, an integration phase 304 and a sample phase 308. The timing diagram is explained in connection with the circuit 200 illustrated in FIG. 2.

During the reset phase 302, the inverting terminal 214 of the primary transconductor 210 is coupled to the ground terminal. An offset associated with the primary transconductor 210 will result in a current flowing from the first output terminal 218 of the primary transconductor 210 to the first capacitor $C_A$ 242.

A corresponding voltage develops at the second input terminal 246 of the secondary transconductor 240 and is stored in the first capacitor $C_A$ 242. Thus, the offset associated with the primary transconductor 210 is stored at an input of the secondary transconductor 240.

Also, in the reset phase 302, the feedback capacitor $C_F$ 212 is charged to the secondary reference voltage signal Vrefs 236. Also, the compensation capacitor Cc 222 is charged to the secondary reference voltage signal Vrefs 236.

The primary capacitor Cp 224 in the switched capacitor network 225 is charged to the primary reference voltage signal Vrefp 238.

In the integration phase 304, the photodiode 202 generates the current signal based on the received light. The integrator 215 receives the current signal from the photodiode 202 at the inverting terminal 214 of the primary transconductor 210. In one version, the integrator 215 receives the current signal from a device coupled to the integrator 215.

The integrator 215 generates an integrated signal at the first output terminal 218 of the primary transconductor 210. The secondary transconductor 240 compensates the offset associated with the primary transconductor 210. The integrator 215 integrates the current signal on the feedback capacitor $C_F$ 212. The feedback capacitor $C_F$ 212 discharges through the photodiode 202. In one version, the feedback capacitor $C_F$ 212 and the compensation capacitor Cc 222 both discharge through the photodiode 202.

The comparator 230 receives the integrated signal from the integrator 215. The comparator 230 is activated by an enable 306 similar to enable signal EN 235 for a defined time period (T). In one example, the defined time period (T) is computed as:

$$T = \frac{Vrefs - Vrefp}{2 \times Vrefs} \quad (8)$$

The comparator 230 compares the integrated signal and the primary reference voltage signal Vrefp 238. If the integrated signal is below the primary reference voltage signal Vrefp 238 during the defined time period, the comparator 230 generates a feedback signal 256. The feedback signal 256 activates the switched capacitor network 225. The feedback signal 256 activates the first input switch S1 226 and the first output switch S2 228. Thus, the primary capacitor Cp 224 is coupled in parallel to the feedback capacitor $C_F$ 212.

If the integrated signal is above the primary reference voltage signal Vrefp 238 during the defined time period, the comparator 230 does not generate the feedback signal 256 and hence, the first input switch S1 226 and the first output switch S2 228 are not activated. In the sample phase 308, the third switch S3 252 and the fourth switch S4 254 are closed, while other switches are in open state. The ADC 250 measures a sampled voltage across the feedback capacitor $C_F$ 212. The ADC 250 generates a digital signal 260 from the sample voltage.

Figure 4:
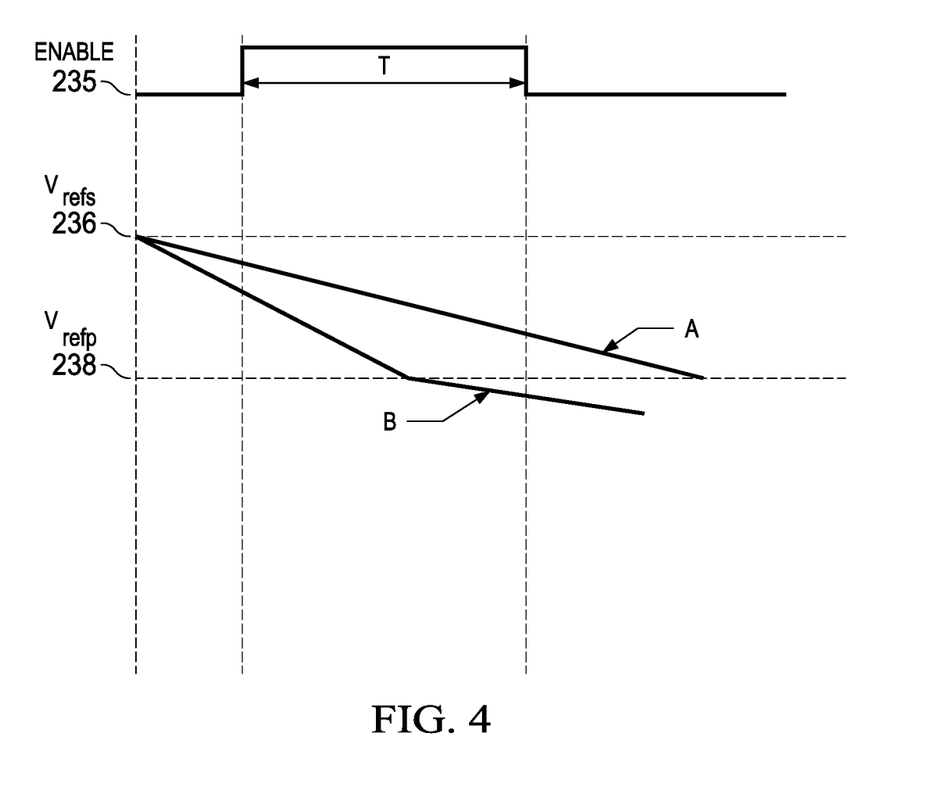
FIG. 4 is a graph to illustrate the operation of the circuit illustrated in FIG. 2, according to an embodiment.

FIG. 4 is a graph to illustrate the operation of the circuit 200, according to an embodiment. The graph is explained in connection with the circuit 200 illustrated in FIG. 2. The graph illustrates an enable signal EN 235. The enable signal EN 235 activates the comparator 230 for a defined time period (T). In one example, the defined time period (T) is computed as:

$$T = \frac{Vrefs - Vrefp}{2 \times Vrefs} \quad (9)$$

In the reset phase, the feedback capacitor $C_F$ 212 is charged to the secondary reference voltage signal Vrefs 236, and the primary capacitor Cp 224 in the switched capacitor network 225 is charged to the primary reference voltage signal Vrefp 238.

In the integration phase, the feedback capacitor $C_F$ 212 starts discharging through the photodiode 202. Graph A illustrates discharge of the feedback capacitor $C_F$ 212. At the beginning of the integration phase (or end of reset phase), the feedback capacitor $C_F$ 212 is charged to the secondary reference voltage signal Vrefs 236. Thus, the integrated signal is equal to the secondary reference voltage signal Vrefs 236. The comparator 230 compares the integrated signal and the primary reference voltage signal Vrefp 238.

As illustrated in Graph A, the integrated signal is above the primary reference voltage signal Vrefp 238 during the defined time period (T). Thus, the comparator 230 does not generate the feedback signal 256 and hence, the first input switch S1 226 and the first output switch S2 228 are not activated.

Graph B illustrates a case when the integrated signal is below the primary reference voltage signal Vrefp 238 during the defined time period (T). The comparator 230 generates a feedback signal 256. The feedback signal 256 activates the switched capacitor network 225. Thus, the primary capacitor Cp 224 is coupled in parallel to the feedback capacitor $C_F$ 212.

The graph B illustrates a change in slope when it reaches the primary reference voltage signal Vrefp 238. This is because when the primary capacitor Cp 224 is coupled in parallel to the feedback capacitor $C_F$ 212, and hence, both discharge through the photodiode 202.

Figure 5:
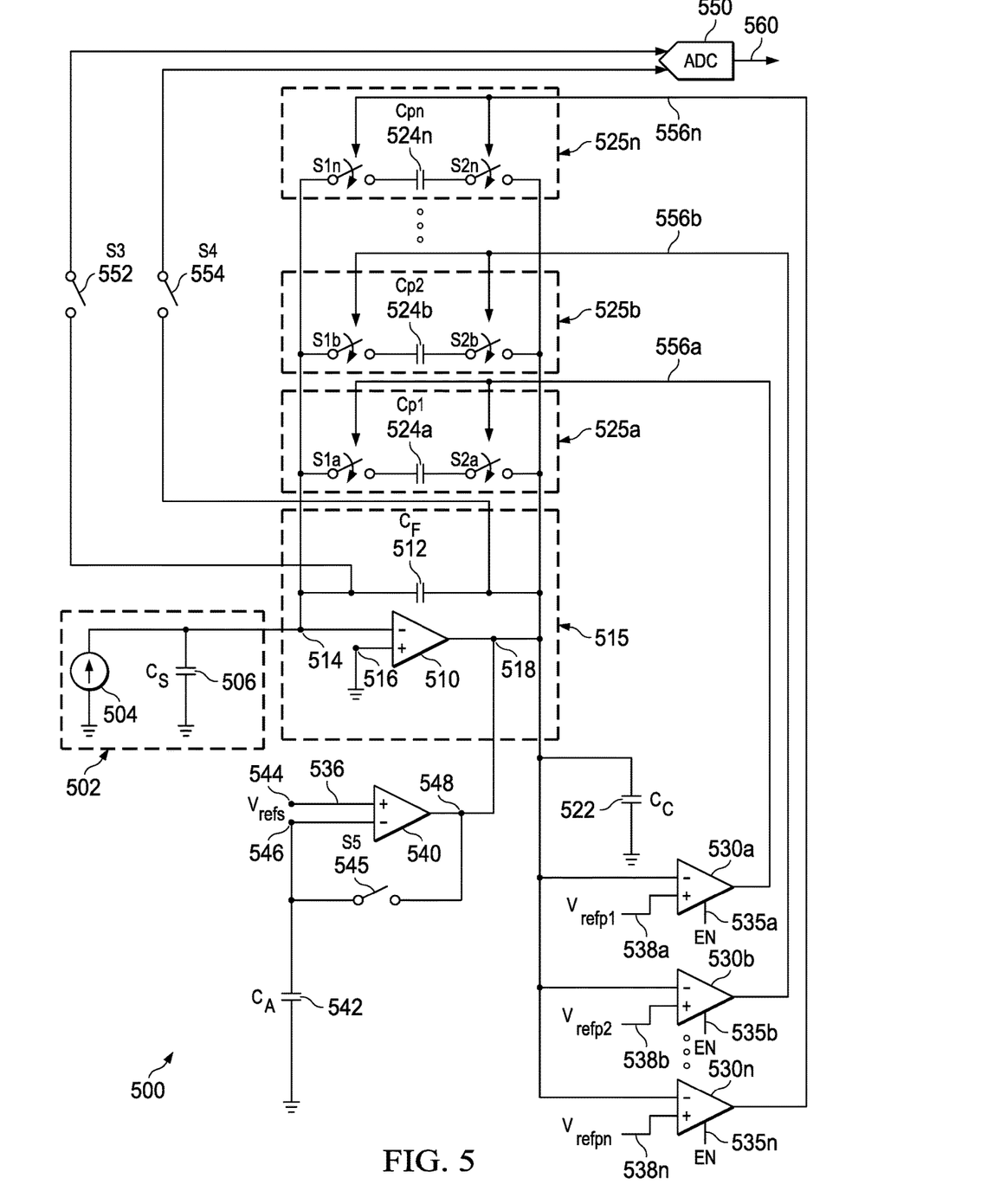
FIG. 5 illustrates a circuit, according to an embodiment.

FIG. 5 illustrates a circuit 500, according to an embodiment. The circuit 500 includes a photodiode 502, an integrator 515, a secondary transconductor 540, and an analog to digital converter (ADC) 550. The circuit 500 includes one or more comparators illustrated as a first comparator 530a, a second comparator 530b and an Nth comparator 530n. The circuit 500 also includes one or more switched capacitor networks illustrated as a first switched capacitor network 525a, a second switched capacitor network 525b and an Nth switched capacitor network 525n.

The photodiode 502 includes a sensor 504 and an associated capacitance Cs 506. The integrator 515 is coupled to the photodiode 502. The integrator 515 includes a primary transconductor 510 with an inverting terminal 514 and a non-inverting terminal 516. The photodiode 502 is coupled to the inverting terminal 514 of primary transconductor 510. A non-inverting terminal 516 of the primary transconductor 510 is coupled to a ground terminal.

A feedback capacitor $C_F$ 512 is coupled between the inverting terminal 514 and a first output terminal 518 of the primary transconductor 510. In one version, the feedback capacitor $C_F$ 512 is also coupled to a secondary reference voltage signal Vrefs 536 and a ground terminal through switches. The ADC 550 is coupled across the feedback capacitor $C_F$ 512 through a third switch S3 552 and a fourth switch S4 554.

The compensation capacitor Cc 522 is coupled to the first output terminal 518 of the primary transconductor 510. In one example, the compensation capacitor Cc 522 is coupled to the secondary reference voltage signal Vrefs 536 through a switch.

The secondary transconductor 540 receives the secondary reference voltage signal Vrefs 536 at a first input terminal 544. A second input terminal 546 of the secondary transconductor 540 is coupled to a first capacitor $C_A$ 542. The other end of first capacitor $C_A$ 542 is coupled to the ground terminal. The second input terminal 546 is coupled to an output terminal 548 of the secondary transconductor through a fifth switch S5 545. The output terminal 548 of the secondary transconductor 540 is coupled to the first output terminal 518 of the primary transconductor 510.

One or more comparators (530a, 530b till 530n) are coupled to the integrator 515. The one or more comparator includes the first comparator 530a, the second comparator 530b and the Nth comparator 530n. A first inverting terminal of each comparator of the one or more comparators is coupled to the first output terminal 518 of the primary transconductor 510. A first non-inverting terminal of the first comparator 530a receives a first primary reference voltage signal Vrefp1 538a. One or more comparators (530a, 530b till 530n) also receive one or more primary reference voltage signals.

A first non-inverting terminal of the second comparator 530b receives a second primary reference voltage signal Vrefp2 538b. Similarly, a first non-inverting terminal of the Nth comparator 530n receives an Nth primary reference voltage signal Vrefpn 538n. Each comparator also receives an enable signal. For example, the first comparator 530a receives an enable signal EN 535a, and the second comparator 530b receives an enable signal EN 535b.

One or more switched capacitor networks are coupled across the integrator 515. The switched capacitor networks are coupled between the inverting terminal 514 and the first output terminal 518 of the primary transconductor. One or more switched capacitor networks include a first switched capacitor network 525a, a second switched capacitor network 525b and an Nth switched capacitor network 525n.

Each of the switched capacitor network of the one or more switched capacitor network includes a first input switch, a first output switch and a primary capacitor Cp coupled between the first input switch and the first output switch. The first input switch is coupled to the inverting terminal 514 of the primary transconductor 510. The first output switch is coupled to the first output terminal 518 of the primary transconductor 510.

For example, the first switched capacitor network 525a includes a first input switch S1a, a first primary capacitor Cp1 524a and a first output switch S2a. Similarly, the second switched capacitor network 525b includes a first input switch S1b, a second primary capacitor Cp2 524b and a first output switch S2b. The circuit 500 may include one or more additional components known to those skilled in the relevant art and are not discussed here for simplicity of the description.

The operation of the circuit 500 illustrated in FIG. 5 is explained now. The operation of the circuit 500 is explained in connection with the first comparator 530a and the second comparator 530b only. Similarly, the first switched capacitor network 525a and the second switched capacitor network 525b are used for depicting the operation of the circuit 500. This eases the understanding of the operation of the circuit 500, and is understood not to limit the scope of the present disclosure.

The photodiode 502 receives light and generates a corresponding current signal. The sensor 504 receives the light and the associated capacitance Cs 506 stores a charge corresponding to the received light. The circuit 500 operates in a reset phase, an integration phase and a sample phase.

In the beginning, all the switches are in open state. In the reset phase, the fifth switch S5 545 is closed. The inverting terminal 514 of the primary transconductor 510 is coupled to the ground terminal. An offset associated with the primary transconductor 510 will result in a current flowing from the first output terminal 518 of the primary transconductor 510 to the first capacitor $C_A$ 542.

A corresponding voltage develops at the second input terminal 546 of the secondary transconductor 540 and is stored in the first capacitor $C_A$ 542. Thus, the offset associated with the primary transconductor 510 is stored at an input of the secondary transconductor 540.

The feedback capacitor $C_F$ 512 is charged to the secondary reference voltage signal Vrefs 536. Also, the compensation capacitor Cc 522 is charged to the secondary reference voltage signal Vrefs 536. The first primary capacitor Cp1 524a in the first switched capacitor network 525a is charged to the first primary reference voltage signal Vrefp1 538a. Similarly, the second primary capacitor Cp2 524b in the second switched capacitor network 525b is charged to the second primary reference voltage signal Vrefp2 538b In the integration phase, the photodiode 502 generates the current signal based on the received light. The integrator 515 receives the current signal from the photodiode 502 at the inverting terminal 514 of the primary transconductor 510. In one version, the integrator 515 receives the current signal from a device coupled to the integrator 515.

The integrator 515 generates an integrated signal at the first output terminal 518 of the primary transconductor 510. The secondary transconductor 540 compensates the offset associated with the primary transconductor 510. The integrator 515 integrates the current signal on the feedback capacitor $C_F$ 512. The feedback capacitor $C_F$ 512 discharges through the photodiode 502. In one version, the feedback capacitor $C_F$ 512 and the compensation capacitor Cc 522 both discharge through the photodiode 502.

One or more comparators receive the integrated signal from the integrator 515. Each comparator is activated by the enable signal EN for a defined time period. For example, the first comparator 530a is activated by the enable signal EN 535a for a first defined time period. In one example, the first defined time period (T1) is computed as:

$$T1 = \frac{Vrefs - Vrefp1}{2 \times Vrefs} \quad (10)$$

Similarly, the second comparator 530b is activated by the enable signal EN 535b for a second defined time period. In another example, the second defined time period (T2) is computed as:

$$T1 = \frac{Vrefs - Vrefp2}{2 \times Vrefs} \quad (11)$$

In one version, Vrefp2 is greater than Vrefp1. One or more comparators (530a, 530b till 530n) generate one or more feedback signals (556a, 556b till 556n). The first comparator 530a compares the integrated signal and the first primary reference voltage signal Vrefp1 538a. If the integrated signal is below the first primary reference voltage signal Vrefp1 538a during the first defined time period (T1), the first comparator 530a generates a feedback signal 556a. The feedback signal 556a activates the first switched capacitor network 525a. The feedback signal 556a activates the first input switch S1a and the first output switch S2a. Thus, the first primary capacitor Cp1 524a is coupled in parallel to the feedback capacitor $C_F$ 512.

If the integrated signal is above the first primary reference voltage signal Vrefp1 538a during the first defined time period (T1), the first comparator 530a does not generate the feedback signal 556a and hence, the first input switch S1a and the first output switch S2a are not activated.

The second comparator 530b compares the integrated signal and the second primary reference voltage signal Vrefp2 538b. If the integrated signal is below the second primary reference voltage signal Vrefp2 538b during the second defined time period (T2), the second comparator 530b generates a feedback signal 556b. The feedback signal 556b activates the second switched capacitor network 525b. The feedback signal 556b activates the first input switch S1b and the first output switch S2b. Thus, the second primary capacitor Cp2 524b is coupled in parallel to the feedback capacitor $C_F$ 512.

If the integrated signal is above the second primary reference voltage signal Vrefp2 538b during the second defined time period (T2), the second comparator 530b does not generate the feedback signal 556b and hence, the first input switch S1b and the first output switch S2b are not activated.

At the end of integration phase, a voltage across the feedback capacitor $C_F$ 522 is a sampled voltage. In the sample phase, the third switch S3 552 and the fourth switch S4 554 are closed, while other switches are in open state. The ADC 550 measures the sampled voltage across the feedback capacitor $C_F$ 522. The ADC 550 generates a digital signal 560 from the sample voltage.

As discussed in connection with circuit 100, illustrated in FIG. 1, the total noise of the circuit is reduced if a value of the feedback capacitor $C_F$ is reduced. This is also illustrated in equations 1 to 6. The circuit 500 provides a low value of the feedback capacitor $C_F$ 512. In one example, the feedback capacitor $C_F$ 512 is 4 pF. Thus, in the integration phase, initially only the feedback capacitor $C_F$ 512 discharges through the photodiode 502.

The integrator 515 generates the integrated signal, and when the integrated signal is below the first primary reference voltage signal Vrefp1 538a, the first primary capacitor Cp1 524a Cp1 also starts discharging through the photodiode 502. Thus, the current signal is integrated at the feedback capacitor $C_F$ 512 and the first primary capacitor Cp1 524a.

If the integrated signal goes even below the second primary reference voltage signal Vrefp2 538b, the second primary capacitor Cp2 524b also starts discharging through the photodiode 502. Thus, the current signal is integrated at the feedback capacitor $C_F$ 512, the first primary capacitor Cp1 524a and the second primary capacitor Cp2 524b.

When a level of the current signal is low, the comparator 530 does not generate the feedback signal, and thus, only the feedback capacitor $C_F$ 512 is part of the circuit 500 in integration phase. This drastically reduces a noise of a system using the circuit 500. The circuit 500, in one embodiment, is used in a data acquisition system to provide variable gain to each detector of the plurality of detectors based on the received current signal.

Figure 6:
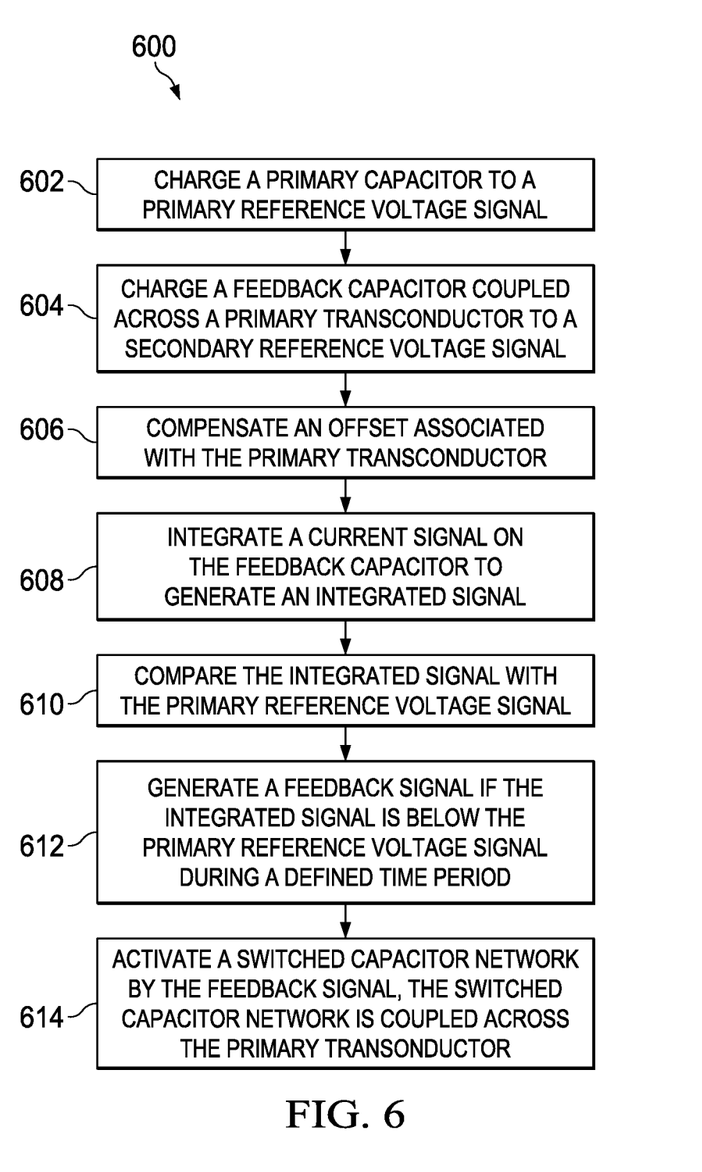
FIG. 6 illustrates a method for generating a digital signal from a current signal, according to an embodiment.

FIG. 6 illustrates a method for generating a digital signal from a current signal, according to an embodiment. At step 602, a primary capacitor is charged to a primary reference voltage signal. As illustrated in circuit 200, the primary capacitor Cp 224 in the switched capacitor network 225 is charged to the primary reference voltage signal Vrefp 238.

At step 604, a feedback capacitor coupled across a primary transconductor is charge to a secondary reference voltage signal. The feedback capacitor $C_F$ 212, in circuit 200, is charged to the secondary reference voltage signal Vrefs 236. At step 606, an offset associated with the primary transconductor is compensated. In one version, the offset associated with the primary transconductor is not taken into account or the step 606 is not performed.

At step 608, a current signal on the feedback capacitor is integrated to generate an integrated signal. In one example, the integrator integrates the current signal on the feedback capacitor. At step 610, the integrated signal is compared with the primary reference voltage signal.

A feedback signal is generated if the integrated signal is below the primary reference voltage signal during a defined time period, at step 612. The defined time period, in an example, is a function of the primary reference voltage signal and the secondary reference voltage signal. At step 614, a switched capacitor network is activated by the feedback signal. The switched capacitor network is coupled across the primary transconductor.

The switched capacitor network includes a primary capacitor. When the feedback signal activates the switched capacitor network, the primary capacitor is coupled in parallel to the feedback capacitor. Thus, initially when the current signal is low, only the feedback capacitor is used for integration. As the current signal increases, the current signal is integrated by both the primary capacitor and the feedback capacitor.

After integration, a voltage across the feedback capacitor is a sample voltage. A digital signal is generated from the sampled voltage. In one example, the ADC generates the digital signal from the sampled voltage.

Figure 7:
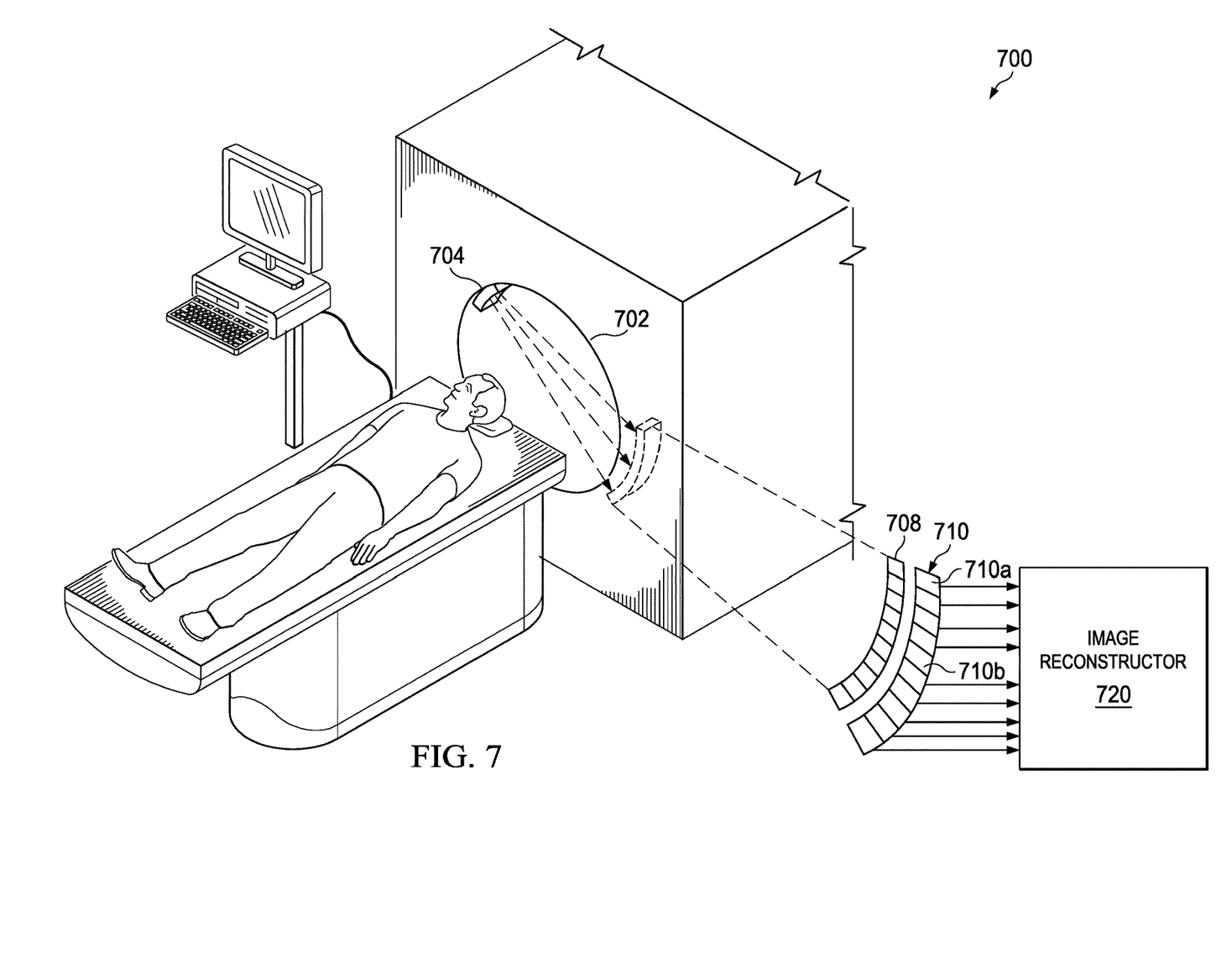
FIG. 7 illustrates an imaging system, according to an embodiment.

FIG. 7 illustrates an imaging system 700, according to an embodiment. The imaging system 700, in one version, is CT a (computed tomography) imaging system. The imaging system 700 includes a gantry 702 that receives a patient. The gantry 702 rotates at a defined speed. In one example, a controller provides the defined speed to the gantry 702.

An x-ray source 704 is disposed in the gantry 702. The x-ray source 704 emits x-rays towards the patient. Many scans are taken progressively as the patient/object is gradually passed through the gantry. A cross-section of the gantry is enlarged and illustrated for better clarity. The cross-section includes a scintillator 708 and a plurality of detectors 710. The scintillator 708 receives x-rays attenuated by the patient. The scintillator 708 generates light from the received attenuated x-rays.

A plurality of detectors 710 is coupled to the scintillator 708. The plurality of detectors 710 includes detectors 710a and 710b. At least one detector of the plurality of detectors 710 include a photodiode and the circuit 200 (illustrated in FIG. 2). The photodiode generates a current signal in response to the received light from the scintillator 708. The circuit 200 is coupled to the photodiode and generates a digital signal, similar to the digital signal 260, based on the current signal received from the photodiode.

The image reconstructor 720 receives the digital signal from each detector of the plurality of detectors 710 to create an image of a part of patient which is being scanned by the imaging system 700. The image reconstructor 720, in one example, includes a processor. The processor can be, for example, a CISC-type (Complex Instruction Set Computer) CPU, RISC-type CPU (Reduced Instruction Set Computer), or a digital signal processor (DSP). The image reconstructor 720, in one example, is disposed outside the imaging system 700.

The circuit 200 provides that a variable gain is provided in each detector of the plurality of detectors 710 based on the current signal generated by the photodiode. This reduces the noise of the imaging system 700 drastically. The imaging system 700 may include one or more additional components known to those skilled in the relevant art and are not discussed here for simplicity of the description.

The foregoing description sets forth numerous specific details to convey a thorough understanding of the invention. However, it will be apparent to one skilled in the art that the invention may be practiced without these specific details. Well-known features are sometimes not described in detail in order to avoid obscuring the invention. Other variations and embodiments are possible in light of above teachings, and it is thus intended that the scope of invention not be limited by this Detailed Description, but only by the following Claims.

What is claimed is:

1. A circuit comprising:
   an integrator configured to generate an integrated signal in response to a current signal;
   a comparator coupled to the integrator and configured to receive the integrated signal and a primary reference voltage signal, the comparator configured to generate a feedback signal; and
   a switched capacitor network coupled across the integrator, wherein the feedback signal is configured to activate the switched capacitor network;
   a feedback capacitor coupled across the integrator;
   an analog-to-digital converter (ADC) coupled across the feedback capacitor; and
   a first transconductor configured to receive a secondary reference voltage signal, and an output terminal of the first transconductor coupled to a first output terminal of the integrator.

2. The circuit of claim 1, wherein the comparator is configured to receive an enable signal, the enable signal configured to activate the comparator for a defined time period.

3. The circuit of claim 1, wherein the integrator comprises:
   a second transconductor configured to receive the current signal at an inverting terminal, and configured to generate the integrated signal at a first output terminal of the integrator;
   a non-inverting terminal of the second transconductor is coupled to a ground terminal; and
   a feedback capacitor coupled between the inverting terminal and the first output terminal of the second transconductor.

4. The circuit of claim 3, wherein the switched capacitor network is coupled between the inverting terminal and the first output terminal of the second transconductor.

5. The circuit of claim 3, the switched capacitor network comprises:
   a first input switch coupled to the inverting terminal of the second transconductor;
   a first output switch coupled to the first output terminal of the second transconductor; and
   a primary capacitor coupled between the first input switch and the first output switch, wherein the first input switch and the first output switch are activated by the feedback signal.

6. The circuit of claim 5 is configured to operate in a reset phase, an integration phase and a sample phase.

7. The circuit of claim 6, wherein in the reset phase:
   the primary capacitor is charged to the primary reference voltage signal;
   the feedback capacitor is charged to the secondary reference voltage signal; and
   the inverting terminal of the second transconductor is coupled to the ground terminal such that an offset associated with the second transconductor is stored at an input of the first transconductor.

8. The circuit of claim 6, wherein in the integration phase:
   the integrator receives the current signal at the inverting terminal of the second transconductor, and generates the integrated signal;
   the first transconductor compensates the offset associated with the second transconductor;
   the comparator is activated by the enable signal for the defined time period; and
   the comparator compares the integrated signal and the primary reference voltage signal, wherein if the integrated signal is below the primary reference voltage signal during the defined time period, the feedback signal is generated by the comparator to activate the first input switch and the first output switch.

9. The circuit of claim 6, wherein in the sample phase the ADC is configured to measure a sampled voltage across the feedback capacitor, the ADC is configured to generate a digital signal from the sampled voltage.

10. A circuit comprising:
    an integrator configured to generate an integrated signal in response to a current signal;
    one or more comparators coupled to the integrator and configured to receive the integrated signal and one or more primary reference voltage signals, the one or more comparators configured to generate one or more feedback signals; and
    one or more switched capacitor networks coupled across the integrator, the one or more switched capacitor networks are activated by the one or more feedback signals;
    a feedback capacitor coupled across the integrator;
    an analog-to-digital converter (ADC) coupled across the feedback capacitor; and
    a first transconductor configured to receive a secondary reference voltage signal, and an output terminal of the first transconductor coupled to a first output terminal of the integrator.

11. The circuit of claim 10, wherein the integrator comprises:
    a second transconductor configured to receive the current signal at an inverting terminal, and configured to generate the integrated signal at a first output terminal;
    a non-inverting terminal of the second transconductor is coupled to a ground terminal; and
    a feedback capacitor coupled between the inverting terminal and the first output terminal of the second transconductor.

12. The circuit of claim 11, wherein each switched capacitor network of the one or more switched capacitor networks comprises:
    a first input switch coupled to the inverting terminal of the second transconductor;
    a first output switch coupled to the first output terminal of the second transconductor; and
    a primary capacitor coupled between the first input switch and the first output switch, wherein the first input switch and the first output switch are activated by a feedback signal of the one or more feedback signals.

13. A method comprising:
    charging a primary capacitor to a primary reference voltage signal;
    charging a feedback capacitor coupled across a primary transconductor to a secondary reference voltage signal;
    compensating an offset associated with the primary transconductor;

integrating a current signal on the feedback capacitor to generate an integrated signal;

comparing the integrated signal with the primary reference voltage signal;

generating a feedback signal if the integrated signal is below the primary reference voltage signal during a defined time period; and activating a switched capacitor network by the feedback signal, wherein the switched capacitor network is coupled across the primary transconductor.

14. The method of claim 13, wherein the switched capacitor network comprises:

a first input switch coupled to an inverting terminal of the primary transconductor;

a first output switch coupled to a first output terminal of the primary transconductor; and a primary capacitor coupled between the first input switch and the first output switch, wherein the first input switch and the first output switch are activated by the feedback signal;

measuring a sampled voltage across the feedback capacitor; and generating a digital signal from the sampled voltage.

15. An imaging system comprising:

a gantry configured to receive a patient, the gantry is configured to rotate at a defined speed;

an x-ray source disposed in the gantry and configured to emit x-rays towards the patient;

a scintillator configured to receive x-rays attenuated by the patient, the scintillator is configured to generate light from the received attenuated x-rays; and a plurality of detectors coupled to the scintillator, at least one detector of the plurality of detectors comprising:

a photodiode configured to generate a current signal in response to received light;

an integrator coupled to the photodiode and configured to generate an integrated signal in response to the current signal received from the photodiode;

a comparator coupled to the integrator and configured to receive the integrated signal and a primary reference voltage signal, the comparator configured to generate a feedback signal; and a switched capacitor network coupled across the integrator, wherein the feedback signal is configured to activate the switched capacitor network, wherein the detector further comprises an analog-to-digital converter (ADC) coupled across the feedback capacitor; and a first transconductor configured to receive a secondary reference voltage signal, and an output terminal of the first transconductor coupled to a first output terminal of the integrator.

* * * * *